United States Patent [19]
Rasch

[11] Patent Number: 5,105,824
[45] Date of Patent: Apr. 21, 1992

[54] URINE SAMPLING DEVICE WITH A FLOAT ACTUATOR

[75] Inventor: Peter Rasch, Ulm-Donau, Fed. Rep. of Germany

[73] Assignee: Wira Limited, Jersey, Channel Islands

[21] Appl. No.: 444,861

[22] Filed: Dec. 4, 1989

[30] Foreign Application Priority Data

Dec. 14, 1988 [GB] United Kingdom ............. 8829203

[51] Int. Cl.[5] .............................................. A61B 5/00
[52] U.S. Cl. ................................................. 128/762
[58] Field of Search ................ 128/760, 762, 767, 771

[56] References Cited

U.S. PATENT DOCUMENTS

| | | | |
|---|---|---|---|
| 3,345,980 | 10/1967 | Ganda | 128/762 |
| 3,499,327 | 3/1970 | Lane | 4/444.1 |
| 3,625,064 | 12/1971 | Hinman, Jr. | 4/444.1 |
| 3,635,091 | 1/1972 | Linzer | 73/421 |
| 3,661,143 | 5/1972 | Henkin | 128/762 |
| 3,722,503 | 3/1973 | Hovick | 128/761 |
| 3,830,107 | 8/1974 | Linzer et al. | 73/421 |
| 3,894,845 | 7/1975 | McDonald | 128/762 |
| 3,943,770 | 3/1976 | McDonald | 73/421 |
| 4,241,017 | 12/1980 | Balistreri et al. | 128/760 |
| 4,305,405 | 12/1981 | Meisch | 128/762 |

FOREIGN PATENT DOCUMENTS

| | | |
|---|---|---|
| 1250581 | 10/1971 | United Kingdom . |
| 1574864 | 9/1980 | United Kingdom . |
| 82/04397 | 12/1982 | World Int. Prop. O. ......... 128/760 |
| WO03213 | 8/1984 | World Int. Prop. O. . |

*Primary Examiner*—Max Hindenburg
*Attorney, Agent, or Firm*—Ladas & Parry

[57] ABSTRACT

The urine sampling device has a receptacle 12 with an inlet 14 for receiving a urine discharge. An outlet from the receptacle leads to a detachable sample container 40. The device includes a mechanism operating automatically upon discharge of an initial fraction or urine to open an initially closed flow passage 62 such that a subsequent, middle fraction of urine is conveyed to the sample container. The final fraction of urine is exhausted to waste.

9 Claims, 3 Drawing Sheets

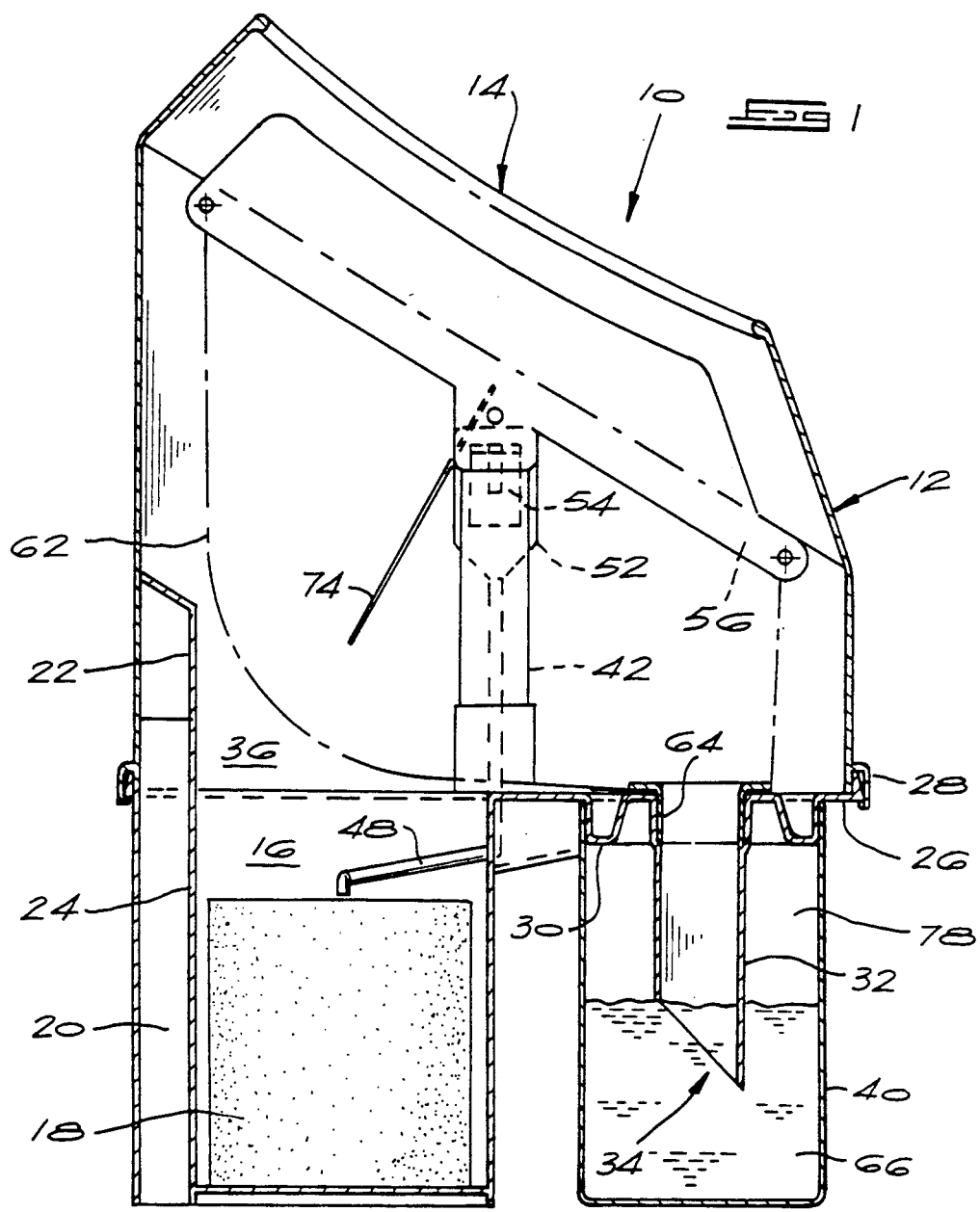
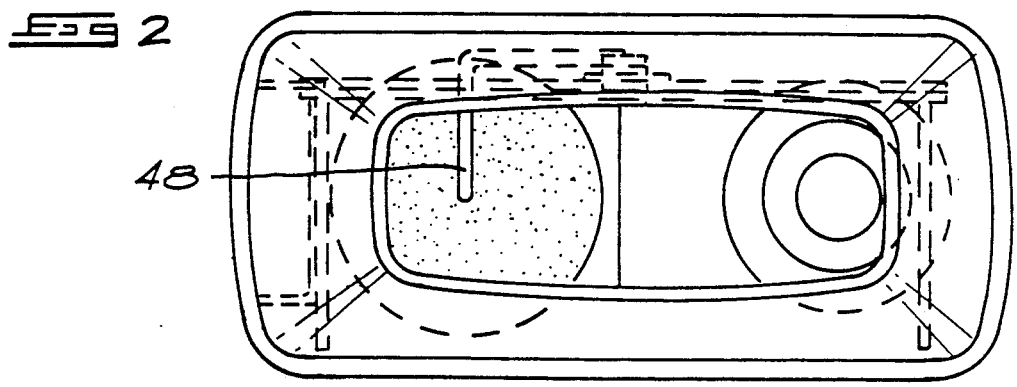

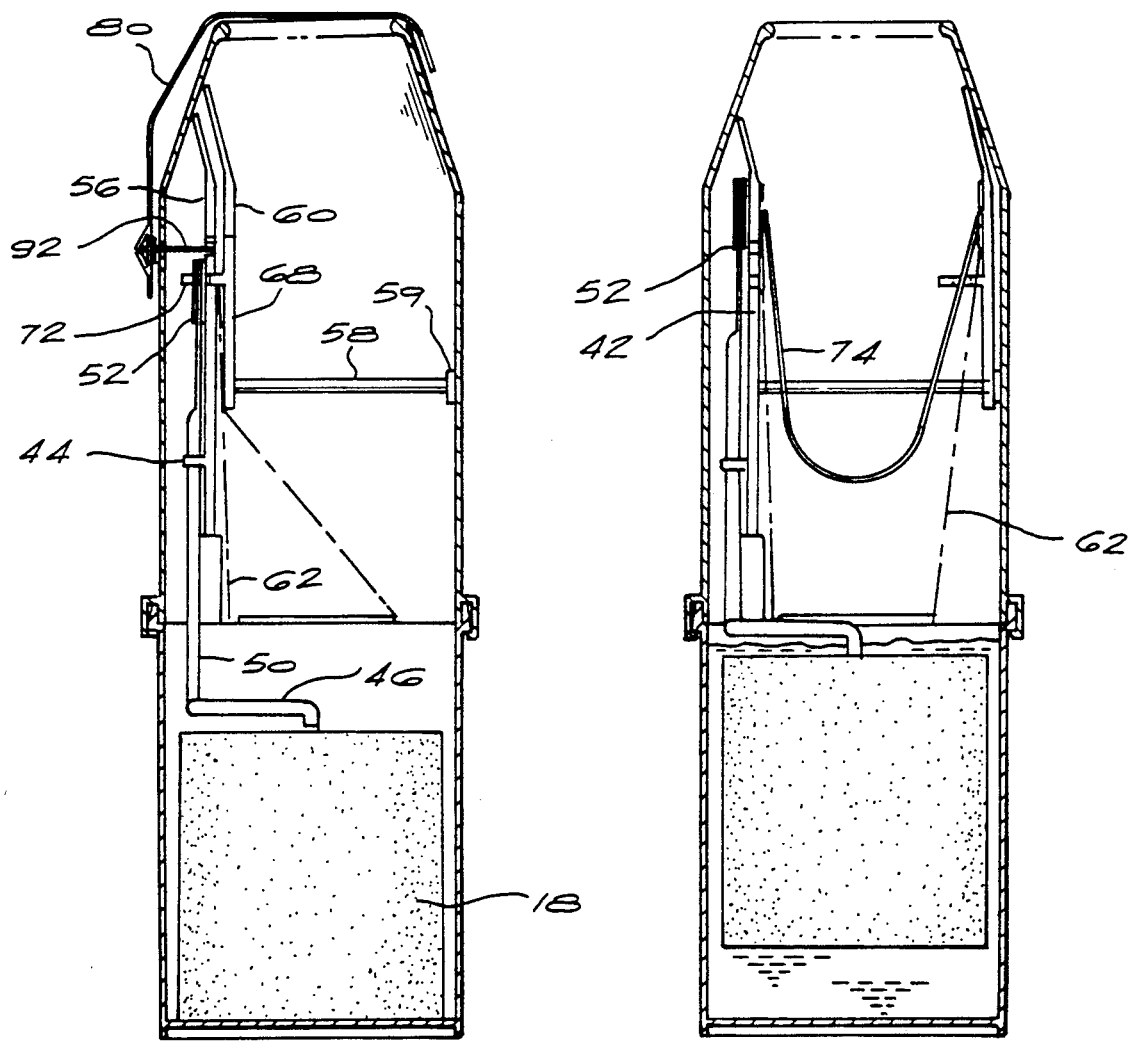

URINE SAMPLING DEVICE WITH A FLOAT ACTUATOR

This invention relates to a urine sampling device.

For accurate medical analysis of urine, it is important that a "middle fraction" of urine be obtained. By this is meant a fraction of the total urine discharge which is neither at the beginning nor at the end of the discharge. It is also important that the middle fraction which is obtained be uncontaminated by the initial discharge.

European patent application No. 79302118.9 (publication No. 0009980) describes a urine sampling device which is designed to capture a middle fraction of the voided urine. The device described in this document has the disadvantage that the middle fraction of urine which is discharged and eventually captured is able to contact the initial fraction both directly and by contacting side walls of the device which have already been contacted by urine in the initial fraction. It is believed that this contamination may render the eventual middle fraction unsuited to accurate medical analysis.

U.S. Pat. No. 3,722,503 also describes a urine sampling device designed to capture a middle fraction of a urine discharge. Once again, urine in the middle fraction can be contaminated by direct contact with urine in the initial fraction and also by contact with the walls of the device previously contacted by the urine of the initial fraction.

British patent 1354001 also addresses the problem of capturing a middle fraction, but again is prone to contamination of the captured fraction by the initial fraction. British patent 1497777 describes a further device intended for the same purpose but in this case requires manual intervention by the user to wet a sponge with urine discharged in the middle fraction.

According to the present invention, there is provided a urine sampling device which comprises a receptacle having an inlet for receiving a urine discharge, an outlet leading in use to a detachable sample container, means operating automatically after an initial fraction of urine has been discharged into the receptacle to open an initially closed flow passage leading to the outlet such that a middle fraction of urine discharged after the initial fraction flows through the flow passage for collection in the container without any substantial contact with parts of the receptacle previously contacted by urine in the initial fraction, and means for separately collecting or exhausting a final fraction of urine discharged after the middle fraction.

Preferably, the flow passage is caused to open automatically by a trigger mechanism once the initial fraction has been discharged into the receptacle. Preferably also, the device comprises a float arranged to float upwardly in the initial fraction of urine and to initiate operation of the trigger mechanism to cause the flow passage to open.

The flow passage may be provided by a funnel having flexible side walls. The funnel may include rigid members attached to the mouth of the funnel and movable from a closed position alongside one another to an open position spaced apart from one another to open the mouth of the funnel. Spring biasing means may be provided to open the funnel in response to operation of the trigger mechanism.

The device may also comprise a detent member operating initially to hold the rigid members in their closed position alongside one another, and an actuator movable in response to upward movement of the float to disable the detent member, thereby freeing the rigid members for movement apart from one another under the bias of the spring biasing means. The flow passage may have an inlet mouth which substantially coincides with the inlet to the receptacle when the flow passage is open. The flow passage may also have an outlet leading into a discharge spout which protrudes in use into the sample container, the discharge spout having an outlet at its operatively lower end.

The invention extends to the combination of a urine sampling device of this kind and a sample container, the container having a mouth dimensioned to make a friction fit with a rib surrounding the discharge spout.

The invention will now be described in more detail, by way of example only, with reference to the accompanying drawings in which:

FIG. 1 shows a cross-sectional view through a urine sampling device according to the invention;

FIG. 2 shows a plan view of the device;

FIG. 3 shows another cross-sectional view of the device prior to operation of the trigger mechanism;

FIG. 4 shows a view similar to that of FIG. 3 after operation of the trigger mechanism;

Figure 5:
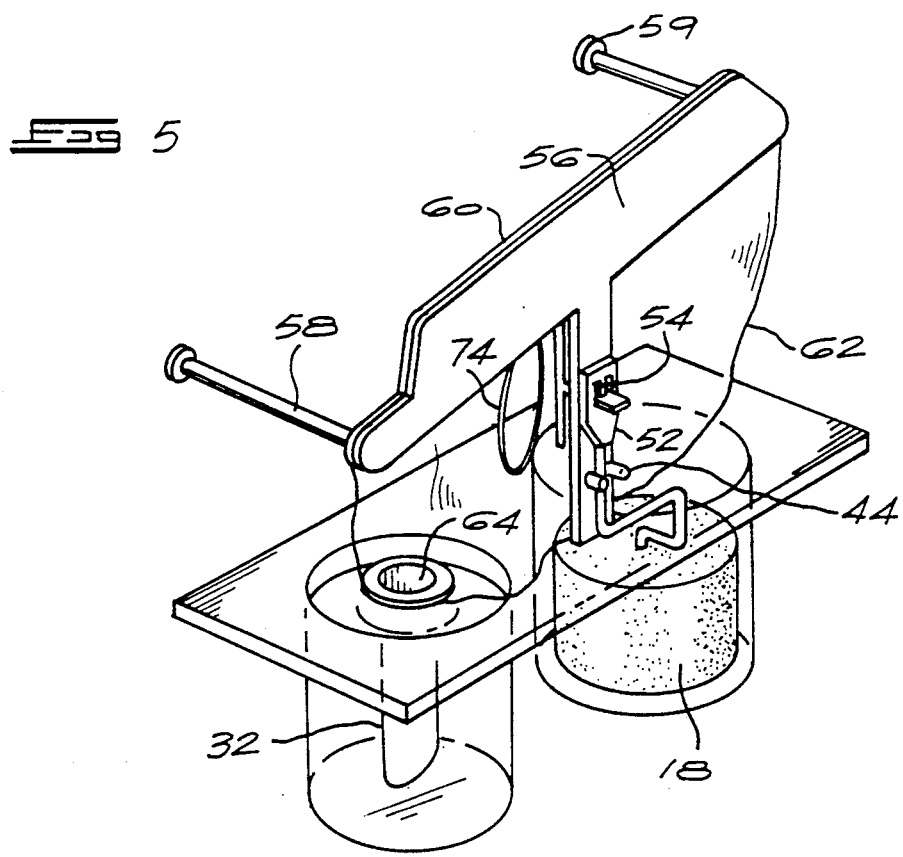
FIG. 5 shows a perspective view of certain parts of the device before operation of the trigger mechanism.

The illustrated urine sampling device 10 has a receptacle 12 moulded in rigid plastics material. The receptacle has an inlet 14 shaped to fit about the urethral opening of a user. Inside the receptacle, there is a float chamber 16 accommodating a loose float 18 with a specific gravity less than that of urine. Next to the float chamber is an overflow passage 20 which communicates with the interior of the receptacle 12 via an overflow 22 defined by a wall 24.

The float chamber 16 depends downwardly from a base 26 of the receptacle with which it is integrally formed. The base 26 has clipping formations 28 by means of which it can be clipped to the upper part of the receptacle 12. The base defines a circular rib 30 and a depending spout 32 which extends downwardly to a chamfered outlet 34. The interior of the float chamber 16 is in fluid communication with the interior 36 of the receptacle 12.

FIG. 1 shows a clear plastics sample container 40 which is attached to the base 26 by frictional engagement of its circular upper edge with the outer periphery of the rib 30. The spout 32 protrudes downwardly into the container as illustrated.

Fixed at its lower end to the base 26 adjacent the float chamber 16 is a post 42 carrying spaced apart guide pins 44. A cranked actuator member has a lower horizontal portion 46 which rests upon the top of the float 18, a cranked portion 48 and a vertical portion 50 connected integrally with the portion 46 via the portion 48. The vertical portion 50 is a vertical slide fit between the guide pins 44 and is accordingly able to move vertically upwardly in response to upward movement of the float 18 in the chamber 16.

At its upper end, the portion 50 carries a detent member 52 in the form of a rigid plate formed with a central cut-out. A pin 54 depends downwardly into the cut-out from the upper edge of the detent member 52.

Spanning across the upper end of the post 42 is a curved member 56 which carries, at its opposite ends, a pair of transverse slide elements 58 formed with abutments 59 at their free ends. Another curved member 60, which has a shape similar to that of the member 56, has holes at it ends through which the elements 58 pass. The member 60 is able to slide relative to the member 56 between the positions seen in FIGS. 5 and 6. In the FIG. 5 position of the member 60, it sits alongside the member 56, while in FIG. 6 position, it is spaced apart from the member 56.

Attached to the members 56 and 60 are the upper edges of a flexible plastics funnel 62.

The funnel tapers inwardly to an outlet at its base, the outlet being defined by a plastics plug 64 locating as a tight fit in an opening formed in the base 26 and leading to the spout 32.

Figure 6:
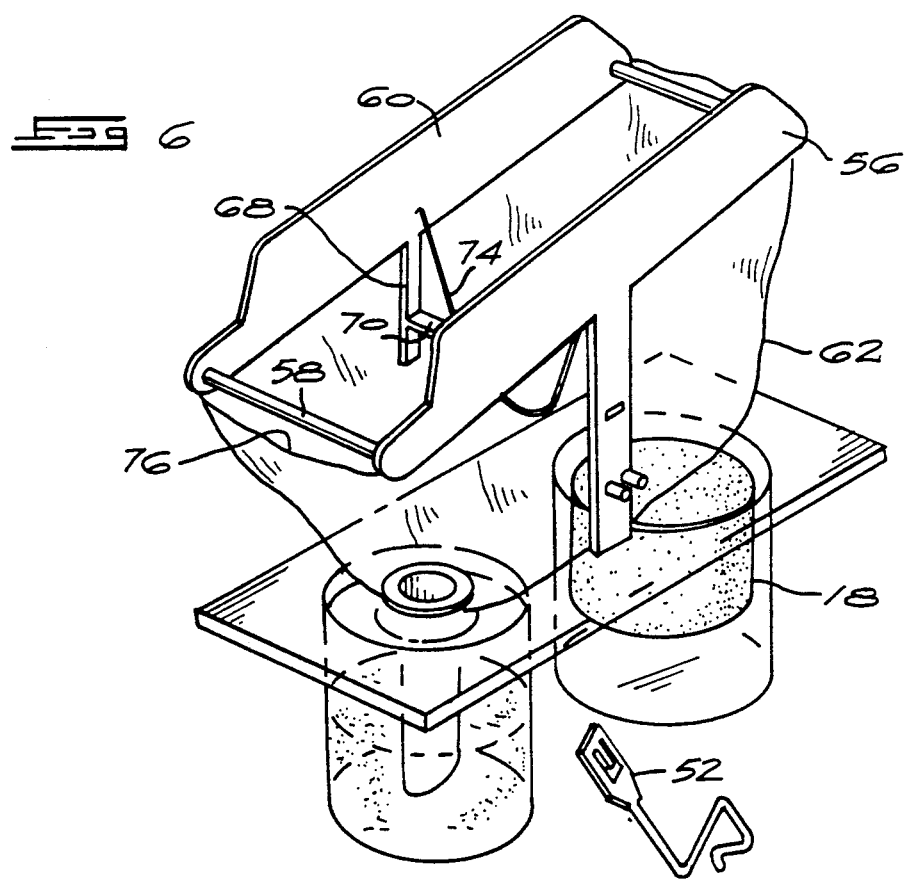
FIG. 6 shows a view similar to FIG. 5, but after operation of the trigger mechanism.

Referring particularly to FIGS. 5 and 6, it will be appreciated that, when the members 56 and 60 are alongside one another (FIG. 5), the entrance to the funnel is closed while when these members are apart (FIG. 6), the entrance to the funnel is open.

A bracket 68 depends downwardly from the member 60 and carries a transverse lug 70 which is formed with a hole 72. With the members 56 and 60 together, the lug 70 protrudes through a slot formed in the post 42 and can be engaged by the pin 54 of the detent member 52. With the pin 54 received in the hole 72, the lug 70 cannot be pulled out of the slot in the post.

A spring element 74 of bowed shape has its ends fastened to the members 56 and 60 at approximately their mid-points. The bias applied by the spring element is such as to urge the member 60 away from the member 56. i.e. from the FIG. 5 to the FIG. 6 position.

In use of the described device, with the member 60 in the FIG. 5 position, the user holds the device such that the inlet 14 is adjacent her urethral opening and commences urinating. With the member 60 in the FIG. 5 position, the funnel 62 is closed, and urine which is initially voided flows into the receptacle 12 and from there into the float chamber 16. The urine level in the chamber 16 builds up, and the float 18 rises. This in turn causes the portion 50 of the cranked actuator member to lift up vertically, raising the detent member 52 and pin 54 as it does so. Eventually, the portion 50 has risen far enough for the pin 54 to disengage from the hole 70, freeing the member 60 from the member 58. Under the bias of the spring element 74, the member 60 moves quickly to the FIG. 6 position to open the funnel 62. Thus the various components constitute a trigger mechanism which operates to open the funnel after a predetermined initial volume of urine has been discharged.

When open, the mouth of the funnel has a size approximately the same as the inner dimensions of the receptacle 12, with the result that subsequently voided urine enters the funnel without any substantial contact with the inner surfaces of the receptacle 12. Thus this urine is substantially uncontaminated by contact with surfaces which have previously been exposed to the initial fraction of voided urine.

The urine flows down the funnel to the outlet defined by the plug 64, and then flows through the outlet into the container 40 via the spout 32. The urine builds up in the container 40 until it covers the chamfered outlet 34, whereafter further urine is unable to flow into the container.

Further urine which is now discharged backs up in the funnel until it reaches the upper edge 76 thereof. The urine overflows the upper edge 76 and accumulates in the bottom of the receptacle 12 with the initially voided fraction which is still inside the receptacle. When the level in the receptacle 12 has risen far enough, the urine is able to overflow into the overflow passage 20. Normally, the sampling procedure will be carried out with the user seated on a toilet seat, so that the overflowing urine can run to waste in the toilet bowl until urination is completed.

The user is now able to invert the whole device over the toilet bowl, with the container 40 still fitted, so that any urine in the receptacle 12 and float chamber 16 can empty to waste.

The level to which the spout 32 protrudes into the container 40 is chosen so that urine 66 in the container will, upon inversion of the device as described, be accommodated in an ullage space 78 above the outlet 34. When the device has been emptied and is righted again, the urine in the space 78 flows back to the bottom of the container 40 which can now be detached from the rib 30 and capped with a suitable cap which seals the captured midstream or middle fraction sample so that it can be handled and transported to a urine testing laboratory. The device 10 itself is then disposed of, although it is conceivable that it could be cleaned and sterilised for re-use.

The major advantage of the invention is that the middle fraction sample is captured entirely automatically and is substantially uncontaminated either by direct contact with the initial fraction of urine or by contact with surfaces of the device previously contacted by the initial fraction. This feature is of course attributable to the fact that the funnel, which is initially closed, is only opened to pass a middle fraction flow once the initial fraction has been voided.

For hermetic reasons, the device 10 may include a lid 80 (FIG. 3) which is releasably attached to the receptacle by means of a safety pin 82. The lid extends over the inlet 14 to prevent ingress of any contaminants into the device prior to use. The lid 80 is removed together with the safety pin 82, thereby freeing the detent member 52 for subsequent upward actuation by the float 18, and rendering the device ready for use.

I claim:

1. A urine sampling device which comprises a receptacle having an inlet for receiving a urine discharge, an outlet leading in use to a detachable sample container, said outlet being normally closed to the passage of urine initially received in said inlet, a float-actuated trigger mechanism operating automatically after an initial fraction of urine has been discharged into the receptacle through the inlet to open by a lateral movement an initially closed flow passage leading to the outlet such that a middle fraction of urine discharged after the initial fraction flows through the flow passage to the outlet for collection in the container without any substantial contact with parts of the receptacle previously contacted by urine in the initial fraction, and means associated with said outlet for separately collecting or exhausting a final fraction of urine discharged after the middle fraction.

2. A urine sampling device according to claim 1 wherein the float of the float-actuated trigger mechanism is arranged to float upwardly in the initial fraction of urine and to initiate operation of the trigger mechanism to cause the flow passage to open.

3. A urine sampling device according to claim 2 wherein the flow passage is provided by a funnel having flexible side walls.

4. A urine sampling device according to claim 3 wherein the funnel includes rigid members attached to the mouth of the funnel and movable from a closed position alongside one another to an open position spaced apart from one another to open the mouth of the funnel.

5. A urine sampling device according to claim 4 comprising spring biasing means to open the funnel in response to operation of the trigger mechanism.

6. A urine sampling device according to claim 5 comprising a detent member operating initially to hold the rigid members in their closed position alongside one another, and an actuator movable in response to upward movement of the float to disable the detent member, thereby freeing the rigid members for movement apart from one another under the bias of the spring biasing means.

7. A urine sampling device according to claim 1 wherein the flow passage has an inlet mouth which substantially coincides with the inlet to the receptacle when the flow passage is open.

8. A urine sampling device according to claim 1 wherein the flow passage has an outlet leading into a discharge spout which protrudes in use into the sample container, the discharge spout having an outlet at its operatively lower end.

9. A urine sampling device according to claim 8 including a rib surrounding the discharge spout, said rib being dimensioned for frictional engagement with a mouth of the sample container whereby the sample container is detachably secured to the device.

* * * * *